US011878139B2

(12) United States Patent
Kim

(10) Patent No.: US 11,878,139 B2
(45) Date of Patent: Jan. 23, 2024

(54) ENDCAP FOR LIQUID MEDICINE-INJECTING TUBE

(71) Applicant: E-WHA MEDITECH INC., Goyang-si (KR)

(72) Inventor: Yong Hyun Kim, Goyang-si (KR)

(73) Assignee: E-WHA MEDITECH INC., Goyang-si (KR)

( * ) Notice: Subject to any disclaimer, the term of this patent is extended or adjusted under 35 U.S.C. 154(b) by 736 days.

(21) Appl. No.: 17/073,999

(22) Filed: Oct. 19, 2020

(65) Prior Publication Data

US 2021/0031022 A1 Feb. 4, 2021

Related U.S. Application Data

(63) Continuation of application No. PCT/KR2019/002890, filed on Mar. 13, 2019.

(30) Foreign Application Priority Data

Apr. 27, 2018 (KR) .......................... 10-2018-0049148

(51) Int. Cl.
*A61M 39/20* (2006.01)
*A61M 39/24* (2006.01)

(52) U.S. Cl.
CPC ............ *A61M 39/20* (2013.01); *A61M 39/24* (2013.01); *A61M 2039/205* (2013.01); *A61M 2205/584* (2013.01); *A61M 2205/7536* (2013.01)

(58) Field of Classification Search
CPC ................. A61M 39/20; A61M 39/24; A61M 2039/205; A61M 2205/584; A61M 2205/7536; A61M 5/385; A61M 2005/1402; A61M 5/165; A61M 5/36
See application file for complete search history.

(56) References Cited

U.S. PATENT DOCUMENTS

| 2005/0203460 A1* | 9/2005 | Kim ...................... A61M 39/20 604/126 |
| 2006/0111667 A1 | 5/2006 | Matsuura et al. |
| 2010/0063445 A1* | 3/2010 | Sternberg .............. A61M 39/20 604/404 |

(Continued)

FOREIGN PATENT DOCUMENTS

| EP | 2 420 276 A2 | 2/2012 |
| KR | 10-0459337 B1 | 12/2004 |
| KR | 10-0463636 B1 | 12/2004 |

(Continued)

OTHER PUBLICATIONS

International Search Report for PCT/KR2019/002890 dated Jun. 17, 2019 (PCT/ISA/210).

*Primary Examiner* — Theodore J Stigell
(74) *Attorney, Agent, or Firm* — Sughrue Mion, PLLC

(57) ABSTRACT

The present invention enables the completion of preparation of liquid medicine injection to be easily and quickly checked with the naked eye based on a color change in an endcap for a liquid medicine-injecting tube. As long as a medical staff checks a color change in the endcap with the naked eye, the medical staff can immediately perform an operation of connecting the tube to a catheter (or injection needle) or the like after removal of the endcap without unnecessarily draining off a large amount of the liquid medicine.

3 Claims, 5 Drawing Sheets

(56) References Cited

U.S. PATENT DOCUMENTS

2015/0283321 A1    10/2015  Dang et al.

FOREIGN PATENT DOCUMENTS

| KR | 10-2017-0047415 A | 5/2017 |
| WO | 02/11791 A1 | 2/2002 |
| WO | 2016/131463 A1 | 8/2016 |
| WO | 2018/009653 A1 | 1/2018 |

* cited by examiner

ENDCAP FOR LIQUID MEDICINE-INJECTING TUBE

CROSS REFERENCE

This application is a Bypass Continuation of International Application No. PCT/KR2019/002890 filed Mar. 13, 2019, claiming priority based on Korean Patent Application No. 10-2018-0049148 filed Apr. 27, 2018, the entire contents of which are incorporated herein by reference.

TECHNICAL FIELD

The present invention relates to an endcap for a liquid medicine-injecting tube by which the completion of preparation of liquid medicine injection can be easily and quickly checked with the naked eye based on a color change in the endcap.

Specifically, the present invention relates to an endcap for a liquid medicine-injecting tube, which enables a user to easily and quickly check, with the naked eye based on a change in the color of an indicator, that the liquid medicine has been introduced into the endcap and "priming", which is a preparatory operation for injection of the liquid medicine into a patient's body, has been completed by removing air existing in the introduced liquid medicine or between portions of the liquid medicine, thereby immediately performing an operation of connecting the tube to a catheter (or an injection needle) or the like without unnecessarily draining off a large amount of the liquid medicine.

Moreover, the present invention relates to an endcap for a liquid medicine-injecting tube, which can prevent a backflow of the liquid medicine toward the tube after the color of an indicator is changed due to contact of the indicator with the liquid medicine, thereby in advance, avoiding unfavorable effects on the liquid medicine contained in the tube.

BACKGROUND ART

A liquid medicine injection apparatus includes a tube for supplying a liquid medicine such as an antibiotic, an analgesic or an anticancer drug, or blood into a human body. An endcap for a liquid medicine-injecting tube is connected to the tube for supplying the liquid medicine into the human body. Before the liquid medicine is injected, a distal end of the tube is blocked by the endcap for the liquid medicine-injecting tube; and when the liquid medicine is injected, the endcap for the liquid medicine-injecting tube is removed and the distal end of the tube is then connected in use to an inlet of a member (for example, a catheter or an injection needle) directly connected to the human body.

In a state where the endcap for the liquid medicine-injecting tube is connected to the tube, a medical staff lowers the liquid medicine so as to remove air that may remain in the tube. As such, a preparatory operation for injection of the liquid medicine into a patient is called "priming." Since a dangerous situation may occur if air enters a patient's body, air that may exist in the tube should be removed in a "priming" process which is a preparatory operation for injection of the liquid medicine into the patient' body.

The endcap for the liquid medicine-injecting tube is a part to be discarded after the "priming" which is a preparatory operation for injection of the liquid medicine into the patient has been completed. After the air that may remain in the tube has been removed by a function of the endcap for the liquid medicine-injecting tube, the endcap for the liquid medicine-injecting tube is detached from the distal end of the tube and the distal end of the tube is connected to a catheter, an injection needle or the like.

However, the determination on whether this priming has been completed depends on experience of a medical staff, and for safety reasons, the liquid medicine is injected into a patient just after a significant amount of the liquid medicine has been drained off. Therefore, loss of the liquid medicine is large in the course of the priming process. In particular, in case of an expensive anticancer drug, a portion of the anticancer drug discarded during the priming process does not come cheap. Thus, this can lead to an economic burden on the patient.

In order to solve the problems mentioned above, an air-removing filter or the like was provided in an endcap coupled to a distal end of a tube in the prior art (see Korean Patent Publication Nos. 10-0459337 and 10-0463636). In order to easily remove air existing in the tube in the prior art, the endcap has the filter, an air vent, and optionally further a liquid-absorbing member. However, this prior art is effective in removing the air existing in the tube, but still has a problem that the determination on a time at which the priming has been completed depends on experience of a medical staff.

That is, even though the conventional endcap of a liquid medicine-injecting tube as described above is excellent technology, continuous improvement can be made thereto like other excellent technologies. For example, in case of a liquid medicine that should be quickly injected into a patient, there is a need for providing a new endcap for a liquid medicine-injecting tube, which enables a user to easily and quickly check, with the naked eye, whether the priming has been completed.

Therefore, an endcap for a liquid medicine-injecting tube according to the present invention relates to a technology which can reduce unnecessary loss of the liquid medicine in the "priming" process (which is a preparatory operation for injection of the liquid medicine into a patient) and can easily and quickly check, with the naked eye, whether the priming has been completed.

Meanwhile, it is to be understood that the matters described as the background art are intended merely to aid in the understanding of the background of the present invention and are not admitted as prior art against the present invention.

SUMMARY

The present invention is conceived to solve the problems of the prior art described above and to provide various additional advantages. An object of the present invention is to provide to an endcap for a liquid medicine-injecting tube by which the completion of preparation of liquid medicine injection can be easily and quickly checked with the naked eye based on a color change in the endcap.

Specifically, an object of the present invention is to provide an endcap for a liquid medicine-injecting tube, which enables a user to easily and quickly check, with the naked eye based on a change in the color of an indicator, that the liquid medicine has been introduced into the endcap for the liquid medicine-injecting tube and "priming", which is a preparatory operation for injection of the liquid medicine into a patient's body, has been completed by removing air existing in the introduced liquid medicine or between portions of the liquid medicine, thereby immediately performing an operation of connecting the tube to a catheter (or an injection needle) or the like without unnecessarily draining off a large amount of the liquid medicine.

Moreover, an object of the present invention is to provide an endcap for a liquid medicine-injecting tube, which can prevent a backflow of the liquid medicine toward the tube after the color of an indicator is changed due to contact of the indicator with the liquid medicine, thereby in advance, avoiding unfavorable effects on the liquid medicine contained in the tube.

However, the objects of the present invention as described above are illustrative and the scope of the present invention is not limited thereby. In addition, other objects and advantages of the present invention will be more apparent from the following description, the appended claims and the accompanying drawings.

These objects are achieved by an endcap for a liquid medicine-projecting tube provided according to the present invention.

An endcap for a liquid medicine-injecting tube provided according to one embodiment of the present invention is an endcap connected to an end of the tube, wherein the endcap for the liquid medicine-injecting tube comprises: a cap main body including a flow passage through which the liquid medicine introduced from the tube flows; a filter member placed in the flow passage and discharging air entrained in the liquid medicine introduced from the tube or air existing between portions of the liquid medicine to an outside of the cap main body so as to remove the air; and an indicator disposed in the cap main body and around the flow passage between the tube and the filter member, wherein the indicator reacts with the liquid medicine flowing in the flow passage so as to exhibit a color when or after the air is discharged to the outside of the cap main body to be removed by the filter member.

In the endcap for the liquid medicine-injecting tube according to one embodiment of the present invention, there is no limitation on the indicator as long as it can react with the liquid medicine flowing in the flow passage so as to exhibit a color and preferably does not contain components harmful to a human body. For example, the indicator may be a litmus paper or a water contact indicator tape. However, it will be apparent that the present invention is not limited thereto and various indicators capable of reacting with the liquid medicine to exhibit a color may be used.

The endcap for the liquid medicine-injecting tube according to one embodiment of the present invention may further comprise a check valve disposed in the flow passage and preventing the liquid medicine, which is introduced from the tube into the cap main body, from flowing backward to the tube. It is preferable that after the indicator comes into contact with and reacts with the liquid medicine so that the color of the indicator is changed, a backflow of the liquid medicine toward the tube is prevented by the function of the check valve, e.g., a one-way valve or a duckbill valve. This is because the liquid medicine introduced into the cap main body reacts with the indicator so that chemical substances are very likely to be contained in the liquid medicine, and if this contaminated liquid medicine flows backward to the tube and is then incorporated into the liquid medicine to be injected into a patient, it may adversely affect the patient.

The endcap for the liquid medicine-injecting tube according to one embodiment of the present invention may further comprise a liquid-absorbing member placed around the flow passage in the cap main body so as to absorb the liquid medicine. In this case, the indicator may be placed between the liquid-absorbing member and an inner wall of the cap main body. Preferably, the indicator may be tightly fixed to the liquid-absorbing member while surrounding the liquid-absorbing member. For example, the liquid-absorbing member may be a sponge member.

In the end cap for the liquid medicine-injecting tube according to one embodiment of the present invention, the filter member may be made of a gas-permeable and liquid-impermeable hydrophobic material. For example, if air exists between portions of the liquid medicine, the liquid medicine which has arrived earlier than the air is absorbed by the liquid-absorbing member having a liquid-absorbing capability before the liquid medicine reaches the filter member. When the liquid medicine introduced earlier than the air has been entirely absorbed by the liquid-absorbing member, the next introduced air reaches the filter member and is then discharged to the outside of the cap main body through the filter member and an air vent formed at an upper end of the cap main body so as to be removed. Accordingly, the filter member having the aforementioned configuration can effectively remove air when the liquid medicine arrives earlier than the air, and prevent the liquid medicine from leaking.

ADVANTAGEOUS EFFECTS

With the configurations described above, the present invention enables the completion of preparation of liquid medicine injection to be easily and quickly checked with the naked eye based on a color change in the endcap for the liquid medicine-injecting tube. The color change in the endcap for the liquid medicine-injecting tube means that the indicator provided in the endcap has reacted with the liquid medicine. That is, this color change, which is a result of the reaction between the indicator and the liquid medicine, enables a medical staff to easily and quickly determine, with the naked eye, that the liquid medicine has flowed into the endcap and that the "priming" process (which is a preparatory operation for injection of the liquid medicine into a patient) has been completed during a time for the reaction between the indicator and the liquid medicine.

Therefore, as long as the medical staff checks a color change in the endcap for the liquid medicine-injecting tube with the naked eye, the medical staff can immediately perform an operation of connecting the tube to a catheter (or an injection needle) or the like after removal of the endcap without unnecessarily draining off a large amount of the liquid medicine.

Moreover, according to the present invention, a backflow of the liquid medicine toward the tube can be prevented after the color of the indicator is changed due to contact of the indicator with the liquid medicine, thereby in advance, avoiding unfavorable effects on the liquid medicine contained in the tube.

It should be understood that the scope of the present invention is not limited to the aforementioned effects.

DETAILED DESCRIPTION

Hereinafter, preferred embodiments according to the present invention will be described in detail with reference to the accompanying drawings. The following embodiments of the present invention are just to implement the present invention and are not intended to limit or restrict the scope of the present invention. Thus, those that can be easily contemplated by persons skilled in the art from the detailed description and examples of the present invention are interpreted to fall within the scope of the present invention. References cited herein are incorporated herein by reference.

Throughout the present specification, it is to be understood that, when any part is referred to as "comprising" any component, it does not exclude other components, but may further include other components, unless otherwise specified.

Generally, an endcap 10 for a liquid medicine-injecting tube according to one embodiment of the present invention is connected to one end of the tube 20, and a liquid medicine injection device is connected to the other end of the tube 20. For example, any of various liquid medicine injection devices, such as a mechanical liquid medicine injection device in which a plunger of a syringe is slowly moved forward by a driving force of a motor so as to push out a liquid medicine filled in a liquid medicine storage space, a balloon type liquid medicine injection device in which a liquid medicine filled in a liquid medicine storage space is slowly pushed out by an elastic restoring force of a balloon, a gas-generating type liquid medicine injection device in which a gas at a certain pressure slowly moves a piston forward so as to push out a liquid medicine filled in a liquid fluid storage space (see Korean Patent Publication No. 10-0507593), or the like, may be connected to the other end of the tube 20. Furthermore, a conventional Ringer solution bottle, a medical fluid bag or the like which injects a liquid medicine to a patient by means of gravity may be used as the liquid medicine injection device.

Figure 1:
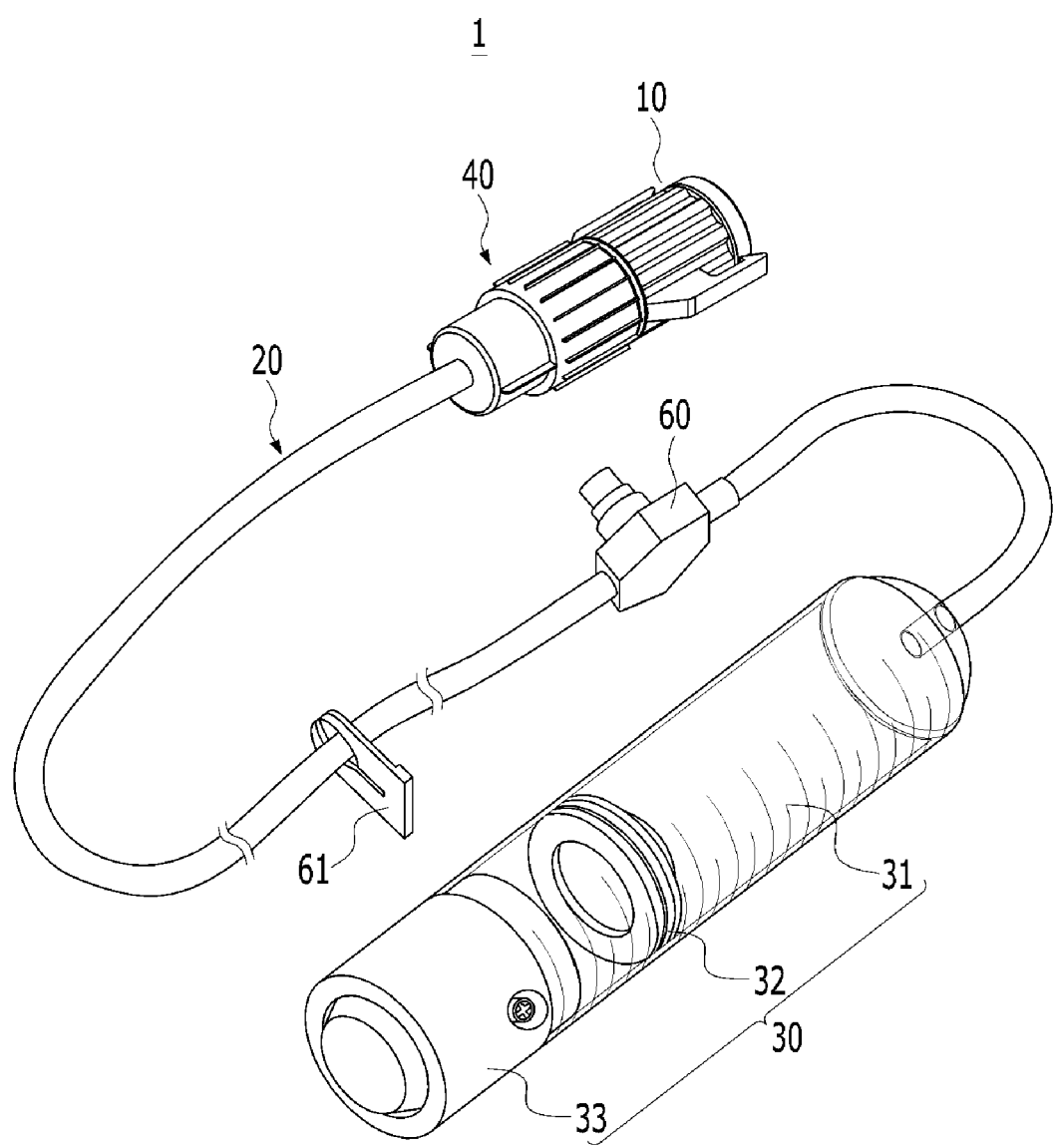
FIG. 1 is an external perspective view illustrating an endcap 10 for a liquid medicine-injecting tube and an injector apparatus 1 including the same, according to one embodiment of the present invention.

As an example that does not limit the present invention, FIG. 1 schematically shows an overall configuration of the endcap 10 for the liquid medicine-injecting tube according to one embodiment of the present invention and an injector apparatus 1 including the same. The injector apparatus 1 according to one embodiment of the present invention includes a liquid medicine injection device 30, the tube 20, an end-connecting member 40, and the endcap 10 for the liquid medicine-injecting tube. As illustrated, the injector apparatus 1 may further include a T-shaped supply valve 60, a clamp 61, and the like.

The liquid medicine injection device 30 of FIG. 1 illustrated only for convenience of description includes a generally cylindrical cylinder 31, a piston 32, and a gas-generating device 33 as main components. The piston 32 is airtightly movable within the cylinder 31, and partitions an internal space of the cylinder 31 into a liquid medicine storage space filled with a liquid medicine (which flows into liquid medicine storage space through the T-shaped supply valve 60 and the tube 20), and a gas-supplying space to which a gas generated in the gas-generating device 33 is supplied. The gas-generating device 33 generates a gas and moves the piston 32 forward by means of a pressure of the generated gas so as to discharge the liquid medicine stored in the liquid medicine storage space to the tube 20. The endcap 10 for the liquid medicine-injecting tube is connected to one end of the tube 20.

The tube 20 is configured to deliver the liquid medicine from the liquid medicine injection device 30 to a patient, and is made of a flexible and transparent or translucent material so that the interior of the tube can be seen by a user. The tube 20 may be provided with the T-shaped supply valve 60 for filling the liquid medicine storage space with the liquid medicine, and the clamp 61 for blocking a flow of the liquid medicine.

The tube 20 is coupled with the end-connecting member 40. The end-connecting member 40 is detachably coupled to the endcap 10 for the liquid medicine-injecting tube. Here, the endcap 10 blocks one end of the tube 20 so as to prevent the liquid medicine from unintentionally leaking. To this end, the end-connecting member 40 is coupled to the end of the tube 20, and the endcap 10 is coupled to the end-connecting member 40 to close the tube 20.

The end-connecting member 40 is normally blocked by the endcap 10. Upon injection of the liquid medicine, a medical staff removes the endcap 10, and connects the end-connecting member 40 to an inlet of a member (for example, a catheter or an injection needle) inserted directly into a human body, to cause the liquid medicine to be injected.

The end-connecting member 40 and the endcap 10 will be described in detail with reference to FIG. 2. The end-connecting member 40 has a cylindrical projection 41 at an end portion thereof. The cylindrical projection 41 is connected to the tube 20 and serves as a pipe to form a passage through which the liquid medicine flows. Although the cylindrical projection 41 is described as having a cylindrical shape, it may be formed to have a polygonal shape such as a triangle, a square or the like, or an elliptical shape.

Furthermore, the end-connecting member 40 has a cylindrical wall 42 surrounding the cylindrical projection 41. The cylindrical wall 42 is formed in a pipe shape, and a center line of the cylindrical wall coincides with or approximately parallel to the cylindrical projection 41. Internal threads are formed on an inner surface of the cylindrical wall 42 to engage with external threads of a bottom boss 111 of the endcap 10 described below, and may threadly engage with a connecting piece of a catheter or the like after the endcap 10 has been removed. These threadly-engaging portions are configured to maintain airtightness well.

Referring to FIGS. 2 to 5, the endcap 10 includes a cap main body 100, optionally a liquid-absorbing member 200, a filter member 300, an indicator 400, and optionally a check valve 500. The endcap 10 is configured to enable an inflow of the liquid medicine from the tube 20 to the endcap, to discharge air (indicated as "a") entrained in the liquid medicine or air 22 present between a portion of the liquid medicine 21 and a portion of the liquid medicine 23 to the outside of the cap main body 100 so as to remove the air, and to prevent the liquid medicine from leaking, thereby performing "priming" which is a preparatory operation for injection of the liquid medicine.

First, the cap main body 100 will be described. The cap main body 100 includes a flow passage 600 through which the liquid medicine flows (see arrows in FIG. 5). The cap main body 100 is connected with the end-connecting member 40 so that the liquid medicine flows from the tube 20 into the cap main body 100. That is, the liquid medicine moves to the flow passage 600 of the cap main body 100 through a passage of the cylindrical projection 41 of the end-connecting member 40 (see FIGS. 2 and 5).

Figure 3:
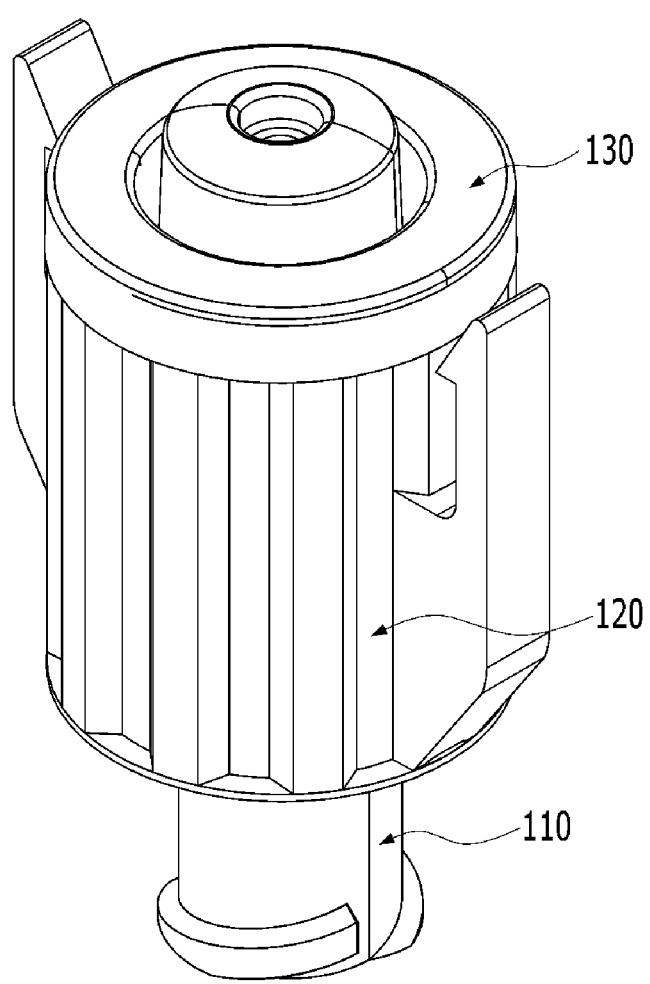
FIG. 3 is an external perspective view of a cap main body 100 according to one embodiment of the present invention.
Figure 4:
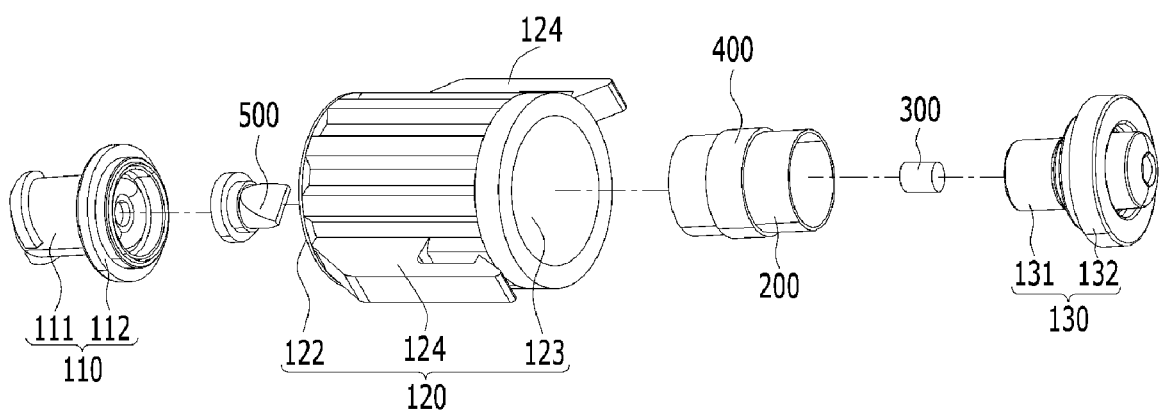
FIG. 4 is an exploded perspective view of the endcap 10 for the liquid medicine-injecting tube according to one embodiment of the present invention.
Figure 5:
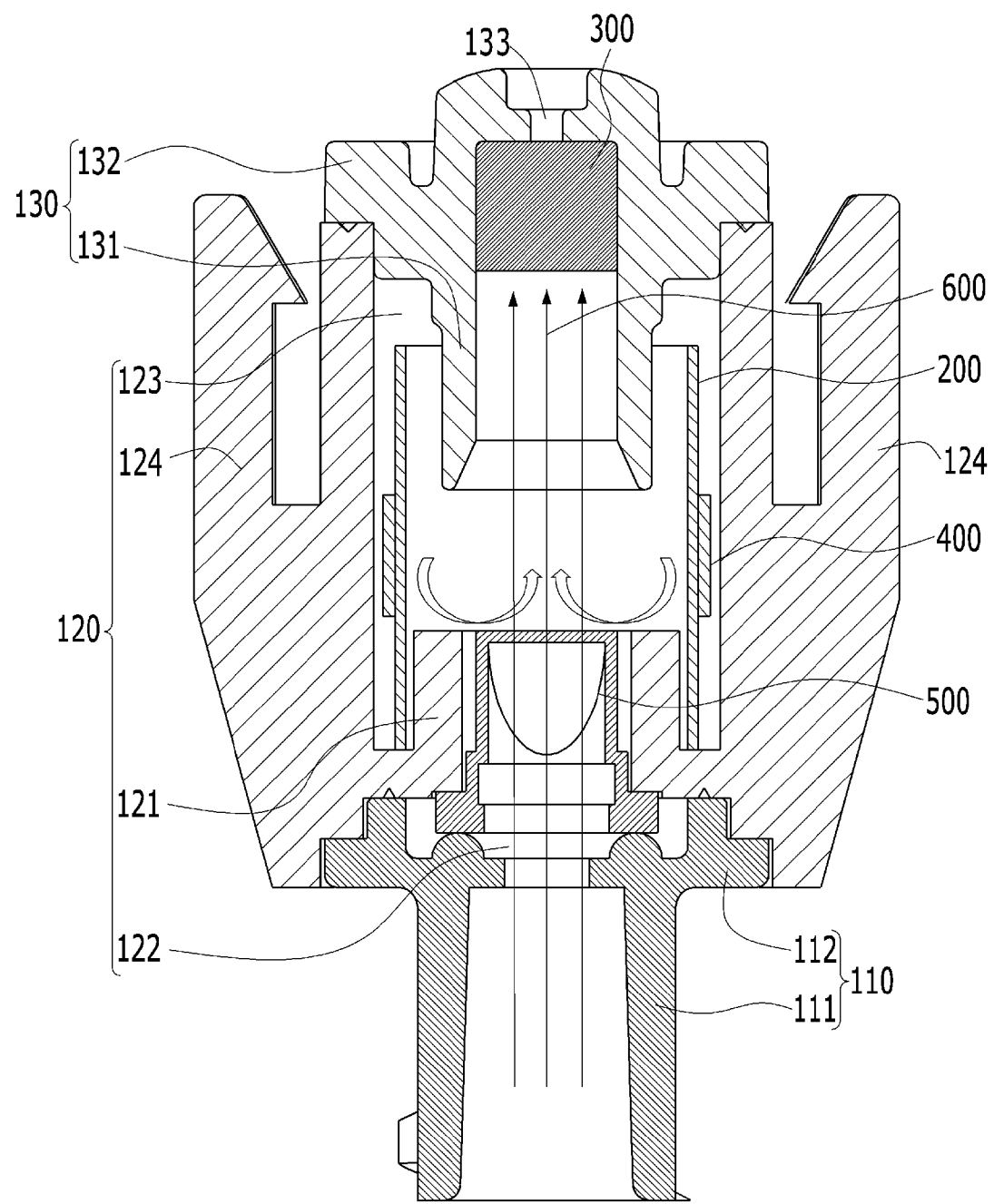
FIG. 5 is a sectional view of the endcap 10 for the liquid medicine-injecting tube according to one embodiment of the present invention.

FIG. 3 illustrates an external perspective view of the cap main body 100 according to one embodiment of the present invention, FIG. 4 illustrates an exploded perspective view of the endcap 10 according to one embodiment of the present invention, and FIG. 5 illustrates a sectional view of the endcap 10 according to one embodiment of the present invention.

Referring to the aforesaid figures, the cap main body 100 may be largely composed of three portions. In more detail, the cap main body includes a lower portion 110, an intermediate portion 120, and an upper portion 130. The flow passage 600 through which the liquid medicine flows is formed through the lower portion 110, the intermediate portion 120, and the upper portion 130.

The lower portion 110 will be described first. The lower portion 110 includes a bottom boss 111 that is a cylindrical portion, and a lower flange 112 extending radially from one end of the bottom boss 111. The inside of the lower boss 111 has an approximate pipe shape, and the flow passage 600 is formed therein.

Furthermore, the lower portion 110 is coupled with the intermediate portion 120, wherein airtight coupling is made to prevent the liquid medicine from leaking. The lower portion 110 is connected to the aforementioned end-connecting member 40, and more particularly, the bottom boss 111 of the lower portion 110 is connected to the cylindrical wall 42 of the end-connecting member 40 by means of thread engagement. Here, the external threads are formed on the outer surface of the bottom boss 111 as described above.

The intermediate portion 120 is formed in a generally cylindrical shape with a handle 124 formed thereon for easy gripping and rotation upon coupling of the intermediate portion to the end-connecting member 40, and has the flow passage 600 formed therein. That is, the inside of the intermediate portion 120 has an approximate pipe shape and includes a lower section 122 and an upper section 123. In addition, the lower portion 110 is coupled to the lower section 122 of the intermediate portion 120, and the upper portion 130 is coupled to the upper section 123 of the intermediate portion 120.

Moreover, the intermediate portion 120 includes an intermediate boss 121. More particularly, the intermediate portion 120 defines the flow passage 600 and includes the intermediate boss 121 extending from a section adjacent to the lower portion 110, i.e., from the lower section 122, towards the interior of the intermediate portion 120. The intermediate boss 121 is spaced apart by a predetermined distance from an inner wall of the intermediate portion 120. A gap exists between the inner wall of the intermediate portion 120 and the intermediate boss 121. The liquid-absorbing member 200 and/or the indicator 400, which will be described later, may be placed in the gap, in such a manner that the liquid-absorbing member 200 and/or the indicator 400 may be firmly supported and secured around the flow passage 600.

The upper portion 130 is coupled to the upper section 123 of the intermediate portion 120. The upper portion 130 includes an upper boss 131 inserted into the intermediate portion 120 and defining the flow passage 600, and an upper flange 132 extending radially from the upper boss 131 and coupled with the intermediate portion 120.

The upper boss 131 is inserted into the intermediate portion 120 to be in communication with the flow passage 600 of the intermediate portion 120 and is spaced apart by a predetermined distance from the inner wall of the intermediate portion 120. An outer diameter of the upper boss 131 is smaller than an inner diameter of the intermediate portion 120. The liquid-absorbing member 200 and/or the indicator 400, which will be described later, may be placed in the space formed between the inner wall of the intermediate portion 120 and the upper boss 131, in such a manner that the liquid-absorbing member 200 and/or the indicator 400 may be firmly supported and secured around the flow passage 600. The filter member 300 is fitted into and coupled to the upper boss 131. An air vent 133 that is in communication with the flow passage 600 is formed at an uppermost end of the upper boss 131. The filter member 300 allows the air (indicated as "a") entrained in the liquid medicine or the air 22 existing between the portion of the liquid medicine 21 and the portion of the liquid medicine 23 to be discharged through the air vent 133 to the outside and thus removed, while preventing the liquid medicine flowing through the flow passage 600 from leaking.

The upper portion 130, the intermediate portion 120, and the lower portion 110 are coupled with one another as illustrated in FIGS. 3 to 5. Among them, airtight coupling is made to prevent the liquid medicine from leaking. The flow passages 600 provided in the upper portion 130, the intermediate portion 120, and the lower portion 110, respectively, are in communication with one another to define one complete flow passage 600.

Next, the liquid-absorbing member 200 will be described. The liquid-absorbing member 200 is an optional structure and is placed around the flow passage 600 to absorb the liquid medicine. The liquid-absorbing member 200 is formed to have a generally cylindrical shape. It is to be understood that the liquid-absorbing member 200 is not limited thereto but may be formed in various shapes.

The liquid-absorbing member 200 is placed around the flow passage 600 of the intermediate portion 120 of the cap main body 100. One end of the liquid-absorbing member 200 is inserted between the inner wall of the intermediate portion 120 and the intermediate boss 121, and the other end thereof is inserted between the inner wall of the intermediate portion 120 and the upper boss 131. Accordingly, the liquid-absorbing member 200 can be stably placed around the flow passage 600.

A material capable of remarkably absorbing and retaining a liquid is preferable for the liquid-absorbing member 200, wherein a foam such as a sponge, a fibrous material such as cloth, or the like may be used for the liquid-absorbing member. However, the material for the liquid-absorbing member 200 in the present invention is not limited thereto. Any material can be employed as long as it absorbs a liquid well.

Meanwhile, the filter member 300 is placed in the flow passage 600 as described above. More particularly, the filter member 300 is placed at or adjacent to the upper portion 130 so as to outwardly discharge the air 22, which has passed through the flow passage 600 around which the liquid-absorbing member 200 is placed. As illustrated, the filter member 300 is placed at the upper portion 130, more particularly, within the upper boss 131. The position of the filter member 300 is not limited thereto but any position is available if the filter member is farther away from the tube 20 than the liquid-absorbing member 200.

The filter member 300 may be made of a gas-permeable and liquid-impermeable hydrophobic material. For example, if the air 22 exists between the portion of the liquid medicine 21 and the portion of the liquid medicine 23, the portion of the liquid medicine 21 which has arrived earlier than the air 22 is absorbed by the liquid-absorbing member 200, which is placed upstream of the filter member 300, around the flow passage 600 before the portion of the liquid medicine 21 reaches the filter member 300 (see FIGS. 2 and 5). When the portion of the liquid medicine 21 introduced earlier than the air 22 has been entirely absorbed by the liquid-absorbing member 200, the next introduced air 22 reaches the filter member 300 via the flow passage 600 and is then discharged to the outside of the cap main body through the air vent 133 and consequently removed.

In order to outwardly discharge the air 22 that has passed through the flow passage 600 surrounded by the liquid-absorbing member 200, the filter member 300 is fitted into the upper boss 131 of the upper portion 130, and the air vent 133 that is in communication with the flow passage 600 is formed at the uppermost end of the upper boss 131. The filter member 300 may be made of a gas-permeable and liquid-impermeable hydrophobic material, and a gas-permeable and liquid-impermeable porous plastic resin material may be processed into a shape suitable for the passage and then used as the filter member. The filter member 300 has some degree of elasticity so that it is slightly contracted while being fitted into the upper boss 131 and then restored to be in place.

Therefore, the liquid-absorbing member 200 and the filter member 300, which have the configurations described above, can effectively remove the air when the portion of the liquid medicine 21 arrives earlier than the air 22, and prevent the liquid medicine from leaking.

Meanwhile, despite the configurations of the liquid-absorbing member 200 and the filter member 300 as described above, the determination on a time at which the priming is completed depends on experience of a medical staff. In other words, the determination on whether the priming has been completed depends on the experience of the medical staff, and for safety reasons, the liquid medicine is injected into a patient just after a significant amount of the liquid medicine has been drained off. Therefore, loss of the liquid medicine is large in the course of the priming process. Accordingly, there is a need for a technology that can reduce unnecessary loss of the liquid medicine in the "priming" process, which is a preparatory operation for injection of the liquid medicine into a patient, and enables a user to easily and quickly check, with the naked eye, whether the priming has been completed.

In response to the technical requirements described above, the indicator 400 provides a function of allowing the medical staff to easily determine whether the priming has been completed.

As an example which does not limit the present invention, the indicator 400 may be connected to the liquid-absorbing member 200. However, it will be apparent that a configuration in which the indicator 400 may be provided alone is not excluded. For example, one end of the indicator 400 may be inserted between the inner wall of the intermediate portion 120 and the intermediate boss 121, and the other end thereof may be inserted between the inner wall of the intermediate portion 120 and the upper boss 131.

As one example, the indicator 400 may be placed between the liquid-absorbing member 200 and the inner wall of the intermediate portion 120 so that the indicator can be stably supported by elasticity of the liquid-absorbing member 200. Preferably, the indicator 400 may be tightly fixed to the liquid-absorbing member 200 while surrounding the liquid-absorbing member 200.

In detail, the indicator 400 is formed in a ring shape or a cylindrical shape to surround the liquid-absorbing member 200 such as a sponge having elasticity. It is to be understood that the present invention is not limited thereto, and the indicator 400 may have the shape of a patch or the like. The indicator 400 is stably placed between the liquid-absorbing member 200 and the inner wall of the intermediate portion 120 by an elastic force of the liquid-absorbing member 200.

The portion of the liquid medicine 21 absorbed by the liquid-absorbing member 200 and then delivered to the indicator 400, or the portion of the liquid medicine 21 delivered directly to the indicator 400 without passing through the liquid-absorbing member 200 reacts with the indicator 400 to exhibit a color. Since it takes a certain time for the indicator 400 to exhibit a color due to the reaction with the portion of the liquid medicine 21, the air 22, which is subsequently introduced, is discharged and removed through the filter member 300 and the air vent 133 to the outside of the cap main body until the color is exhibited. Therefore, as long as the medical staff checks a color change in the endcap with the naked eye based on a change in the color of the indicator 400, the medical staff is able to find that the preparatory process for injection of the liquid medicine has been completed, whereby an operation of connecting the tube to a catheter (or an injection needle) or the like can be immediately performed after removal of the endcap 10 without unnecessarily draining off a large amount of the liquid medicine.

The indicator 400 may include a material of which color is changed when at least a part of the portion of the liquid medicine 21 is delivered thereto. For example, the indicator 400 may include a water contact indicator tape, a litmus paper, or the like which is initially white in color but is changed to red in color when it comes into contact with a liquid. However, the indicator 400 is not limited thereto but may have any configuration as long as it exhibits a certain color or a change in color upon reaction thereof with the liquid medicine.

Meanwhile, at least a part of the cap main body 100 is made of a transparent or translucent material such that the medical staff can check a change in the color of the indicator 400. In particular, at least a part of the intermediate portion 120 is formed of a transparent or translucent material.

Figure 2:
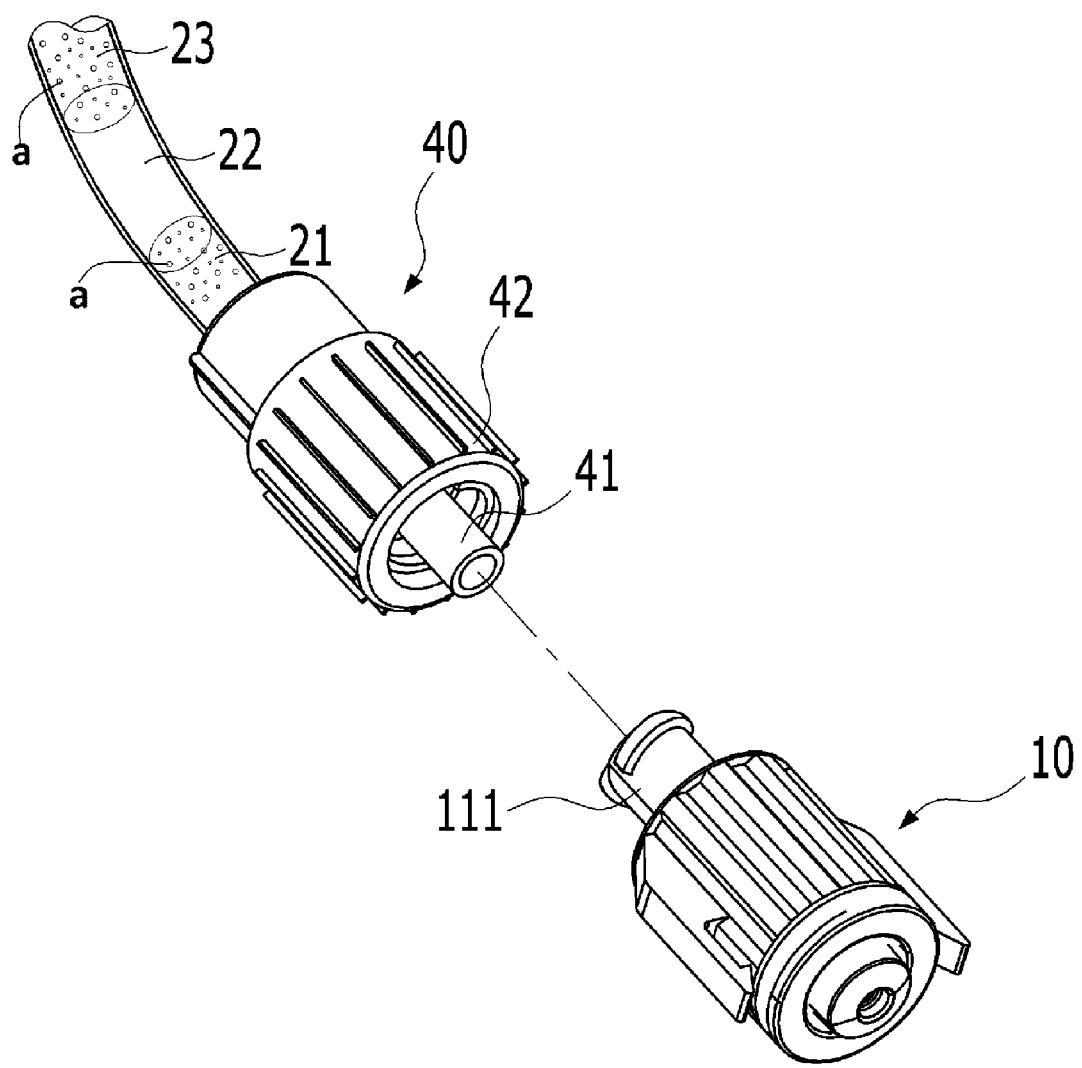
FIG. 2 is an enlarged partial perspective view illustrating a state where the endcap 10 for the liquid medicine-injecting tube according to one embodiment of the present invention is coupled to a distal end of the tube 20.

Referring to FIG. 2, in the tube 20, the air 22 exists immediately behind the portion of the liquid medicine 21 that first reaches an end of the tube 20. Then, the portion of the liquid medicine 21 flows into the endcap 10 through the passage of the end-connecting member 40.

The portion of the liquid medicine 21 that has been first introduced is entirely absorbed by the liquid-absorbing member 200 having a liquid-absorbing capability before the portion of the liquid medicine 21 reaches the filter member 300. At this time, some of the portion of the liquid medicine 21 absorbed by the liquid-absorbing member 200 is delivered to the indicator 400.

The portion of the liquid medicine 21 that has been absorbed by the liquid absorbing member 200 does not flow into the filter member 300; or even though it flows into the filter member 300, it does not pass through the filter member 300 due to the hydrophobicity of the filter member 300. When the portion of the liquid medicine 21 that has been first introduced is entirely absorbed by the liquid-absorbing member 200, the next introduced air 22 entirely escapes the cap main body 100 through the filter member 300 and the air vent 133, and as a result, only the portion of the liquid medicine 23 which is subsequently introduced remains within the cap main body 100.

Then, as long as the medical staff checks, with the naked eye, a color change due to a reaction of the indicator 400 with some of the portion of the liquid medicine 21, which has been delivered to the indicator 400, the medical staff is able to find that the preparatory process for injection of the liquid medicine has been completed. Therefore, the medical staff is able to connect the tube to the catheter or the like after he/she easily removes the endcap 10 without unnecessarily wasting a large amount of the liquid medicine.

Meanwhile, the indicator 400 may include a substance such as color-changeable reagent, and this substance may flow backward to the tube 20. If the substance flows backward as such, there is a concern that the substance such as a reagent may be injected into a patient and there is also a concern that unknown adverse effects may occur. In order to avoid these problems, the endcap 10 may optionally further include the check valve 500.

The check valve 500 is disposed in the flow passage 600 of the cap main body 100 and prevents a backflow of the liquid medicine that has been introduced into the cap main body 100. The check valve 500 is placed at the lower section 122 of the intermediate portion 120 of the cap main body 100. Specifically, the check valve 500 is placed within the intermediate boss 121. It is to be understood that the present invention is not limited thereto and the check valve 500 may be placed at the lower portion 110.

As illustrated in FIG. 5, the check valve 500 is a one-way valve for preventing a backflow of the liquid medicine that has been introduced into the cap main body 100, and prevents a backflow of the liquid medicine to the tube 20 after the color of the indicator 400 is changed due to contact with the liquid medicine, thereby in advance, preventing unfavorable effects on the liquid medicine within the tube. As one example, the check valve 500 may be a duckbill valve.

Although the present invention has been described with reference to the embodiments, the scope of the present invention is not limited to these embodiments. Any person skilled in the art will appreciate that various modifications and changes are possible without departing from the spirit and scope of the present invention and these modifications and changes also fall within the scope of the present invention.

I claim:

1. An endcap for a liquid medicine-injecting tube, the end cap being connected to an end of the tube, comprising:
a cap main body comprising a flow passage through which a liquid medicine introduced from the tube flows;
a filter member placed in the flow passage and discharging air entrained in the liquid medicine introduced from the tube or air existing between portions of the liquid medicine to an outside of the cap main body so as to remove the air;
a liquid-absorbing member placed in the cap main body and around the flow passage between the tube and the filter member so as to absorb the liquid medicine; and
an indicator disposed in the cap main body and around the flow passage between the tube and the filter member, the indicator being tightly fixed to the liquid-absorbing member while surrounding the liquid-absorbing member, and being stably placed between the liquid-absorbing member and an inner wall of the cap main body by an elastic force of the liquid-absorbing member, wherein the indicator reacts with the liquid medicine which flows in the flow passage and is absorbed by the liquid-absorbing member and delivered to the indicator so as to exhibit a color when or after the air is discharged to the outside of the cap main body to be removed by the filter member.

2. The endcap of claim 1, further comprising a check valve disposed in the flow passage and preventing the liquid medicine introduced from the tube into the cap main body from flowing backward to the tube.

3. The endcap of claim 1, wherein the indicator is a litmus paper or a water contact indicator tape.

* * * * *